US007644889B2

(12) United States Patent  (10) Patent No.: US 7,644,889 B2
Johnson (45) Date of Patent: Jan. 12, 2010

(54) FLUID SENSING SYSTEM AND METHODS, INCLUDING VEHICLE FUEL SENSORS

(75) Inventor: Roger F. Johnson, Bellevue, WA (US)

(73) Assignee: Insitu, Inc., Bingen, WA (US)

( * ) Notice: Subject to any disclaimer, the term of this patent is extended or adjusted under 35 U.S.C. 154(b) by 60 days.

(21) Appl. No.: 11/489,075

(22) Filed: Jul. 18, 2006

(65) Prior Publication Data

US 2008/0017758 A1  Jan. 24, 2008

(51) Int. Cl.
 *G01F 23/28* (2006.01)
 *G01F 23/284* (2006.01)
 *B64D 37/02* (2006.01)

(52) U.S. Cl. ..................... 244/135 R; 73/293

(58) Field of Classification Search .............. 73/112, 73/113, 118.1, 290 R, 291, 29; 244/135 B, 244/136, 1 R, 135 R, 135 C; 342/124; 250/357.1
See application file for complete search history.

(56) References Cited

U.S. PATENT DOCUMENTS

| 3,389,602 | A | * | 6/1968 | Clemens ............... 73/290 R |
| 3,713,338 | A | * | 1/1973 | Kind ...................... 73/293 |
| 3,794,428 | A | * | 2/1974 | Giesecke ................ 356/434 |
| 3,908,441 | A | * | 9/1975 | Virloget ................ 73/54.08 |
| 4,051,726 | A |   | 10/1977 | Hastbacka |
| 4,107,993 | A | * | 8/1978 | Shuff et al. ............ 73/290 R |
| 4,287,427 | A | * | 9/1981 | Scifres .................. 250/577 |
| 4,396,911 | A | * | 8/1983 | Motsinger et al. ......... 340/617 |
| 4,410,886 | A | * | 10/1983 | Motsinger ............... 340/617 |
| 4,450,722 | A |   | 5/1984 | Keyes, IV et al. |
| 4,904,878 | A |   | 2/1990 | Gipp et al. |
| 4,954,724 | A | * | 9/1990 | Koda et al. .............. 250/577 |
| 5,073,720 | A |   | 12/1991 | Brown |
| 5,274,245 | A |   | 12/1993 | Lee |
| 5,889,284 | A |   | 3/1999 | Mattis |
| 6,274,880 | B1 | * | 8/2001 | Walker .................. 250/577 |
| 6,293,143 | B1 | * | 9/2001 | Denton et al. ............. 73/293 |
| 6,333,512 | B1 |   | 12/2001 | Wirthlin |
| 6,546,794 | B2 | * | 4/2003 | Kim et al. ............... 73/290 V |

(Continued)

OTHER PUBLICATIONS

International Search Report; PCT Application No. PCT/US07/69134; Applicant: Insitu, Inc.; Date of Mailing: Nov. 14, 2007; 1 page.

(Continued)

*Primary Examiner*—Michael R Mansen
*Assistant Examiner*—Joseph W Sanderson
(74) *Attorney, Agent, or Firm*—Perkins Coie LLP

(57) ABSTRACT

Fluid sensing systems and methods, including sensors used to sense various fluid levels in vehicles, are disclosed herein. One aspect of the invention is directed toward a method for sensing a fluid that includes passing electromagnetic radiation through a receptacle positioned to hold a fluid. The receptacle can be configured so that electromagnetic radiation that passes through portions of the receptacle containing fluid is focused. The method can further include determining (a) whether fluid is located in a selected portion of the receptacle based on an amount of electromagnetic radiation that impinges on at least one radiation sensor, (b) a characteristic of fluid located in the passageway of the selected portion based on a pattern of the electromagnetic radiation that is created on the at least one radiation sensor, or (c) both (a) and (b).

24 Claims, 7 Drawing Sheets

U.S. PATENT DOCUMENTS

| | | |
|---|---|---|
| 6,668,645 B1 | 12/2003 | Gilmour et al. |
| 6,801,678 B2 | 10/2004 | Murshid |
| 6,925,871 B2 | 8/2005 | Frank et al. |
| 7,113,125 B2 * | 9/2006 | Le Sesne .................... 342/124 |
| 7,121,507 B2 | 10/2006 | Dennis et al. |
| 7,162,922 B2 * | 1/2007 | Freger et al. .............. 73/290 V |
| 7,199,388 B2 * | 4/2007 | Omatoi ....................... 250/573 |

OTHER PUBLICATIONS

International Written Opinion for International Patent Application No. PCT/US07/69134, Applicant: The Insitu Group., mailed on Dec. 12, 2007, 9 pages.

* cited by examiner

FLUID SENSING SYSTEM AND METHODS, INCLUDING VEHICLE FUEL SENSORS

TECHNICAL FIELD

Embodiments of the present invention relate to fluid sensing systems and methods, including sensors used to sense various fluid levels in vehicles.

BACKGROUND

During aerospace vehicle operations, knowing the amount of fuel the vehicle carries can be critical. For example, when a vehicle operates over an extended range or period of time, small variations in fuel consumption can determine whether the vehicle will be safely recovered or lost. Accordingly, various methods for determining the amount of fuel carried by an aerospace vehicle have been developed.

For example, some aerospace vehicles monitor engine fuel flow during the operation of an aerospace vehicle to determine the amount of fuel used over time. The amount of fuel used is subtracted from the total amount of fuel that was loaded on the vehicle prior to departure to provide an estimation of the amount of fuel remaining. A drawback of this method is that certain malfunctions cannot be detected. For example, a fuel leak would not be detected by the fuel flow indicators unless the leak occurs past the point were fuel flow was measured. Accordingly, an aerospace vehicle with an undetected fuel leak can run out of fuel even though the computed fuel remaining (based on the fuel flow indicators) indicates that the aerospace vehicle is still carrying a sufficient amount of fuel to continue to its recovery point.

Another method of determining the amount of fuel remaining in an aerospace vehicle during flight is to install pressure sensors in the fuel tank(s) of the vehicle. These pressure sensors measure the column pressure of the fuel in the corresponding tank. In many cases, a companion pressure sensor that measures atmospheric pressure is required to compensate for changes in column pressure due to changes in altitude. A drawback of these systems is that they are often large, bulky, and heavy. Additionally, these systems can require electrical components to be in contact with the fuel. In some cases, if these electrical components are exposed to fuel vapors, they can elevate the risk of explosion.

DETAILED DESCRIPTION

A. Introduction

Figure 1:
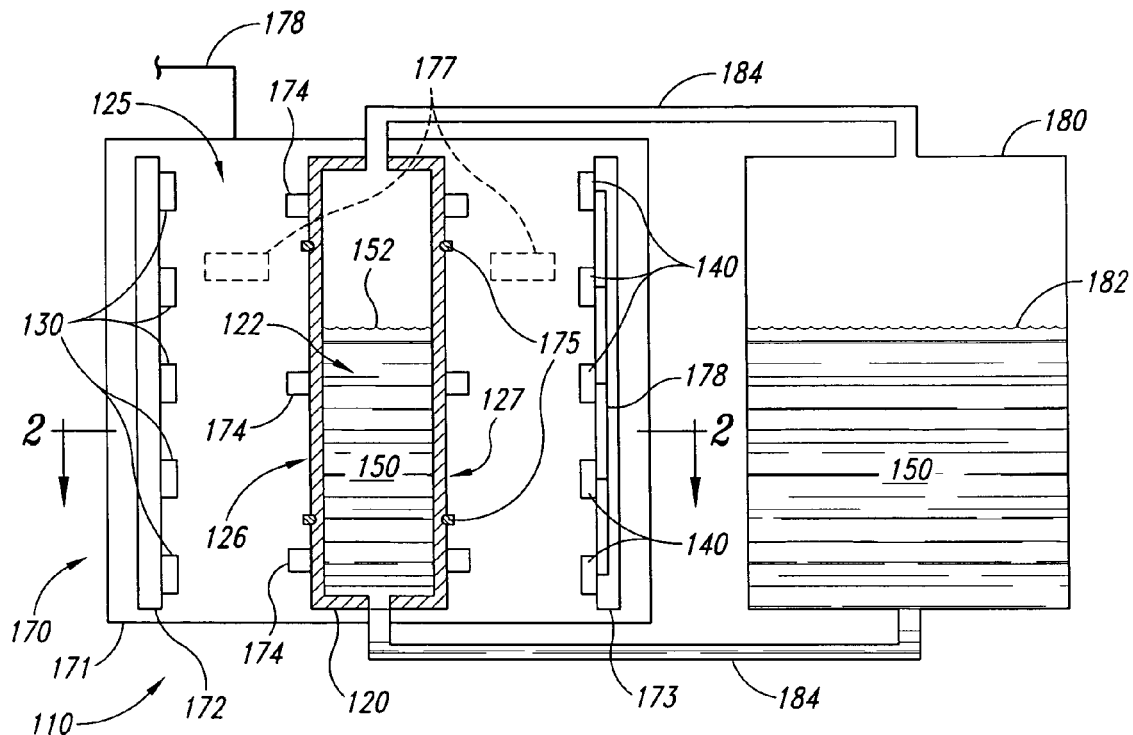
FIG. 1 is a partially schematic side elevation of a fluid sensing system in accordance with embodiments of the invention.

The present invention is directed generally toward fluid sensing systems and methods. Aspects of the invention are directed toward a fluid sensing system that includes a receptacle having a passageway for containing a fluid. The system can further include at least one radiation source positioned to emit electromagnetic radiation through the receptacle. The system can still further include at least one radiation sensor positioned to receive a portion of the emitted electromagnetic radiation that passes through the receptacle. The receptacle can be configured so that electromagnetic radiation that passes through portions of the receptacle containing fluid is focused to impinge on the radiation sensor so that more emitted electromagnetic radiation is received by the radiation sensor through portions of the receptacle that contain fluid than through portions that do not contain fluid.

Other aspects of the invention are directed toward a fluid sensing system that includes a receptacle having a passageway for containing a fluid. The system can further include at least one radiation source positioned to emit electromagnetic radiation through the receptacle. The system can still further include at least one radiation sensor positioned to receive a portion of the emitted electromagnetic radiation that passes through the receptacle. The receptacle can be configured so that electromagnetic radiation that passes through portions of the receptacle containing fluid is focused to create a pattern on the radiation sensor. The pattern can be dependent on a characteristic of the fluid.

Still other aspects of the invention are directed toward a fluid sensing system that includes means for passing electromagnetic radiation through a receptacle having a passageway for holding a fluid. The receptacle can be configured so that electromagnetic radiation that passes through portions of the receptacle containing fluid is focused. The system can further include means for determining (a) whether fluid is located in a selected portion of the receptacle based on an amount of electromagnetic radiation that impinges on at least one radiation sensor after passing through the selected portion of the receptacle, (b) a characteristic of fluid located in the passageway of the selected portion based on a pattern of the electromagnetic radiation that is created on the at least one radiation sensor after passing through the selected portion of the receptacle, or (c) both (a) and (b).

Yet other aspects of the invention are directed toward methods for sensing a fluid that includes passing electromagnetic radiation through a receptacle that has a passageway for holding a fluid. The receptacle can be configured so that electromagnetic radiation that passes through portions of the receptacle containing fluid is focused. The method can further include determining (a) whether fluid is located in a selected portion of the receptacle based on an amount of electromagnetic radiation that impinges on at least one radiation sensor after passing through the selected portion of the receptacle, (b) a characteristic of fluid located in the passageway of the selected portion based on a pattern of the electromagnetic radiation that is created on the at least one radiation sensor after passing through the selected portion of the receptacle, or (c) both (a) and (b).

Still other aspects of the invention are directed toward a method for making a fluid sensing system that includes positioning at least one radiation source to emit electromagnetic radiation through a receptacle that has a passageway for containing a fluid. The receptacle can be configured so that electromagnetic radiation that passes through portions of the receptacle containing fluid is focused. The method can further include positioning at least one radiation sensor to receive a portion of the emitted electromagnetic radiation that passes through the receptacle to determine (a) whether fluid is located in a selected portion of the receptacle based on an amount of electromagnetic radiation that impinges on at least one radiation sensor after passing through the selected portion of the receptacle, (b) a characteristic of fluid located in the passageway of the selected portion based on a pattern of the electromagnetic radiation that is created on the at least one radiation sensor after passing through the selected portion of the receptacle, or (c) both (a) and (b).

B. Fluid Sensing System and Associated Methods

The present disclosure describes fluid sensing systems and methods, including sensors used to sense various fluid levels in vehicles. Several specific details of the invention are set forth in the following description and in FIGS. 1-18 to provide a thorough understanding of certain embodiments of the invention. One skilled in the art, however, will understand that the present invention may have additional embodiments, and that other embodiments of the invention may be practiced without several of the specific features described below.

Figure 2:
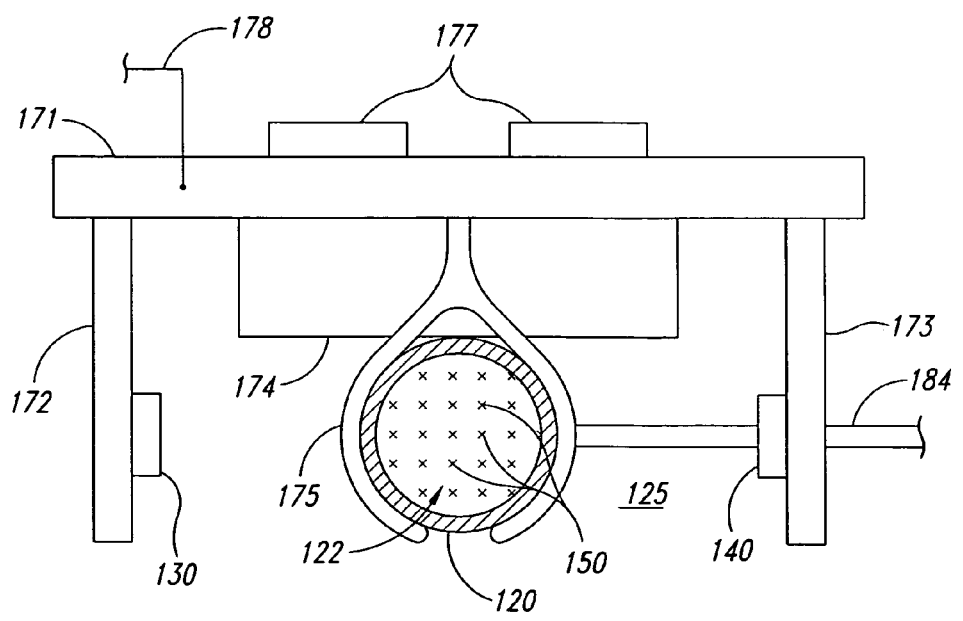
FIG. 2 is a partial schematic cross-sectional illustration of a portion of the fluid sensing system shown in FIG. 1 taken along line 2-2.

FIG. 1 is a partially schematic side elevation of a fluid sensing system 110 in accordance with embodiments of the invention. FIG. 2 is a partially schematic cross-sectional illustration of a portion of the fluid sensing system 110 shown in FIG. 1 taken along line 2-2. In FIG. 1, the fluid sensing system 110 includes a receptacle 120 positioned proximate to one or more radiation sources 130 and one or more radiation sensors 140. In the illustrated embodiment, the receptacle 120 includes a first side 126 and a second side 127. The first and second sides 126, 127 can be positioned to form or carry a passageway 122, which can be suitable for containing a fluid 150 (e.g., a liquid, gas, suspension, or other fluid with a suitable refractive index). In the illustrated embodiment, the receptacle 120 includes a hollow cylinder or tube and the radiation sources 130 and the radiation sensors 140 are positioned exterior to the receptacle 120. In other embodiments, the fluid sensing system 110 can have other arrangements, including a receptacle 120 with a different shape or radiation sources 130 and radiation sensors 140 with different locations.

The passageway 120 of the fluid sensing system 110 can be in fluid communication with a fluid tank or container 180 via connectors 184. Because the connectors 184 connect the bottom of the container 180 to the bottom of the receptacle 120 and the top of the container 180 to the top of the receptacle 120, a fluid 150 (e.g., a fuel) can flow between the container 180 and the passageway 122 of the receptacle 120. Accordingly, the fluid level 152 in the receptacle 120 can be at least approximately the same as the fluid level 182 in the tank 180. As described below in further detail, in various embodiments the radiation sources 130 can emit electromagnetic radiation (e.g., one or more selected wavelengths of light) and a fluid level and/or a fluid characteristic of the fluid in the passageway 120 can be determined by the characteristics of the emitted electromagnetic radiation received by the radiation sensors 140. In turn, a fluid level and/or a characteristic of the fluid in the container 180 can also be determined.

Referring to FIGS. 1 and 2, the receptacle 120 is carried on a support structure 170. In the illustrated embodiment, the support structure 170 includes a first support 171, a second support 172, and a third support 173. The first support 171 carries the receptacle 120 using holding devices 175 and spacers 174. The first support 171 can also carry the second and third supports 172, 173. In turn, the second support 172 can carry the radiation sources 130 and the third support 173 can carry the radiation sensors 140. In the illustrated embodiment, the first, second, and third supports 171, 172, 173 include printed circuit boards which can carry electronic signal paths and/or connections for the radiation sources 130 and the radiation sensors 140. In other embodiments, the support structure 170 can have other arrangements (e.g., more or fewer circuit boards).

Additionally, in selected embodiments the first, second, and/or third supports 171, 172, 173 can carry other electronic devices 177, as shown in FIG. 2. For example, as discussed below in further detail, the other electronic devices can include one or more of a controller, a processor, a transimpedance converter, an analog to digital converter, and the like. At least one of the first, second, and third supports 171, 172, 173 can be operably coupled to a signal path 178, which can be configured to carry an output from the fluid sensing system 110 to another system or component and/or to provide electrical power to the fluid sensing system 110.

In the illustrated embodiment, the receptacle 120 includes a material that allows selected wavelengths of electromagnetic radiation to pass through the first and second sides 126, 127 (e.g., the receptacle can be transparent to selected wavelengths of light). Additionally, the receptacle 120 can be configured so that when electromagnetic radiation 160 passes through a portion of the receptacle 120 that contains the fluid 150, at least a portion of the electromagnetic radiation 160 is focused to impinge on at least one of the radiation sensors 140. For example, FIG. 3 is a partially schematic planform illustration of a portion of the fluid sensing system shown in FIG. 1, including one of the radiation sources 130, one of the radiation sensors 140, and a portion of the receptacle 120 that contains the fluid 150.

Figure 3:
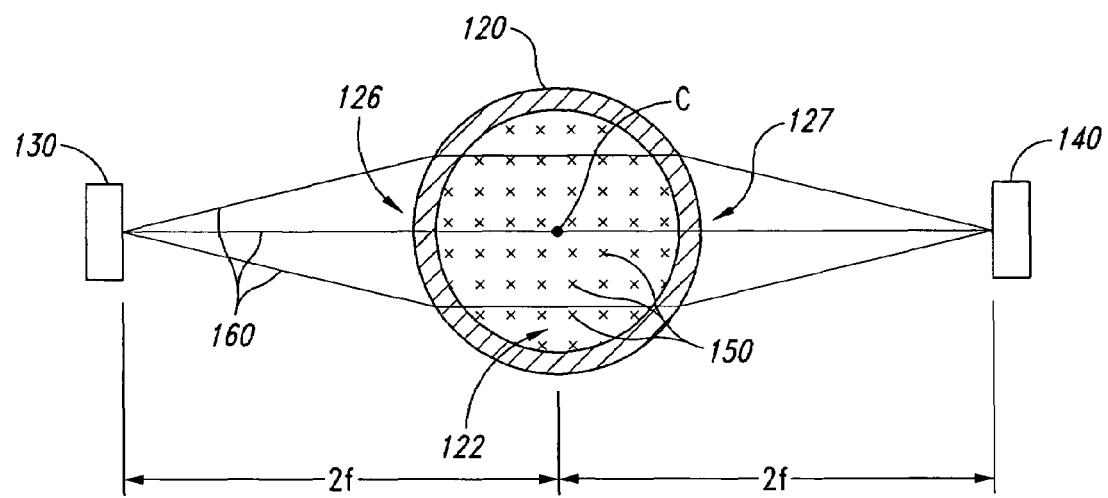
FIG. 3 is a partially schematic planform illustration of a radiation source, a radiation sensor, and a portion of a receptacle that contains a fluid shown in FIG. 1.

When the portion of the receptacle 120 shown in FIG. 3 contains the Fluid 150, it can act as a cylindrical lens that causes certain types of electromagnetic radiation to converge (e.g., to be focused). For example, in the illustrated embodiment, the radiation source 130 can include a quasi-point electromagnetic radiation source that emits a cone of electromagnetic radiation 160 (e.g., light) with an angle of from about 20° to about 60°. For example, the radiation source 130 can include a Light Emitting Diode ["LED"] or a laser diode that produces a quasi-point source approximately 100 times smaller than the outer diameter of the receptacle 120. The radiation source 130 can be positioned at least approximately two focal lengths f from the center C of the passageway 122. In other embodiments, the radiation sources 130 can have other configurations (e.g., other sizes and/or characteristics).

In the illustrated embodiment, the radiation sensor 140 can be configured and positioned to receive the emitted electromagnetic radiation 160. For example, the radiation sensor 140 can include a photodiode, a photo transistor, a Charge Coupled Device ["CCD"], a Charge-Injection Device ["CID"], a CCD array, and/or a CID array that provides an output based on the amount of electromagnetic radiation 160 it receives. In FIG. 3, the radiation sensor 140 can be positioned at least approximately two focal lengths f from the center C of the passageway 122 opposite the radiation source 130, so that the electromagnetic radiation 160 is focused toward, proximate to, or on the radiation source 130 when the portion of the receptacle 120 contains fluid 150 that has a selected optical refractive index (e.g., a refractive index of about 1.3 to about 2.0). It will be understood by those skilled in the art that electromagnetic radiation 160 being focused toward or proximate to the radiation sensor 140 (e.g., with a focal plane located on the radiation sensor 140, or near the radiation sensor 140, but located in front or behind the radiation sensor 140) can cause at least a portion of the electromagnetic radiation 160 to converge toward the radiation sensor 140. Accordingly, a larger amount of the emitted electromagnetic radiation 160 can impinge on and be captured by the radiation sensor 140 (e.g., wherein the radiation sensor 140 has a selected size) when the emitted electromagnetic radiation 160 is focused toward the radiation sensor 140 as compared to when the emitted electromagnetic radiation 160 is not focused toward the radiation sensor 140.

Figure 4:
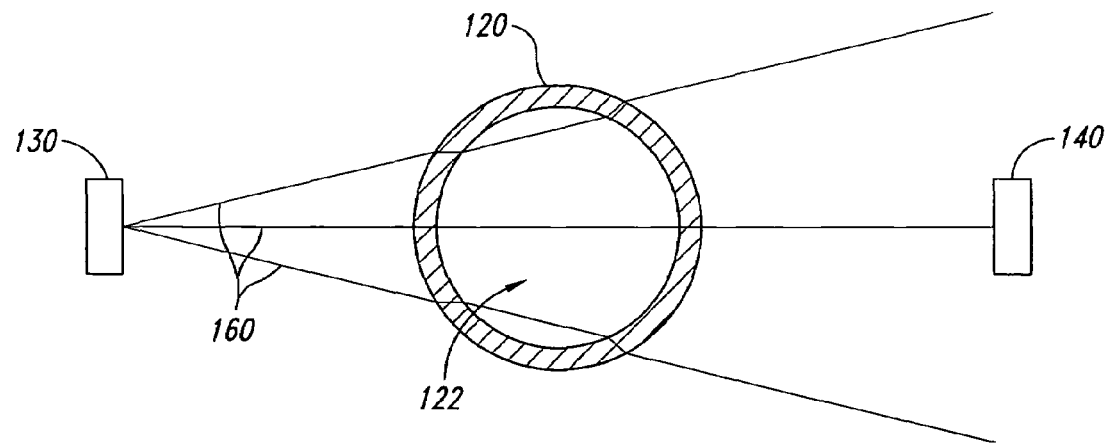
FIG. 4 is a partially schematic planform illustration of the radiation source, the radiation sensor, and the portion of the receptacle shown in FIG. 3 without the fluid.

FIG. 4 is a partially schematic planform illustration of the radiation source 130, the radiation sensor 140, and the portion of the receptacle 120 shown in FIG. 3 without the fluid 150. As shown in FIG. 4, when the portion of the receptacle 120 does not contain a fluid, portions of the electromagnetic radiation 160 emitted by the radiation source 130 diverge as they pass through the receptacle 120. Accordingly, a smaller amount of emitted electromagnetic radiation 160 impinges on the radiation sensor 140 when the receptacle 120 does not contain the fluid 150 than when the portion of the receptacle 120 contains the fluid 150.

Referring back to FIG. 1, the multiple radiation sources 130 and radiation sensors 140 can be used to determine where in the receptacle 120 fluid is present and absent, which in turn can be used to determine a fluid level 152 in the passageway 122 of the receptacle 120 and the fluid level 182 in the container 180. For example, in the illustrated embodiment at least one of the other electronic components 177 includes a controller (e.g., a decoder or matrix addressing device) that is operably coupled to the individual radiation sources 130 (e.g., the radiation sources 130 can be connected to the controller in parallel). The controller can be configured to individually activate or turn on the radiation sources 130 and individually deactivate or turn off the radiation sources 130.

In operation, each radiation source 130 can be activated sequentially and the output of one or more corresponding radiation sensors 140 can be used to determine if a portion of the receptacle 120 proximate to the activated radiation source 130 contains the fluid 150. For example, in the illustrated embodiment a single dedicated radiation sensor 140 is positioned to receive emitted radiation from a corresponding individual radiation source 130. When the radiation sensor 140 receives electromagnetic radiation from its associated radiation source 130, the radiation sensor 140 can provide an output based on the amount of electromagnetic radiation that impinges on the radiation sensor 140. For example, the output of the radiation sensor 140 can be an electrical current and/or a change in an electrical current characteristic of an electrical circuit that is coupled to the radiation sensor (e.g., a change in voltage, amperage, impedance, or the like). In the illustrated embodiment, the radiation sensors 140 can be coupled to the processor in series or in parallel.

In certain embodiments, at least one of the other electronic components 177 can include a processor that processes the output of the radiation sensors 140. For example, in selected embodiments the processor can include a signal processor (e.g., a processor that converts an analog signal to a digital signal and/or creates a pulse width modulated signal for carrying data). In other embodiments, the processor can determine the fluid level 152 (e.g., an air/liquid interface) in the passageway 122 of the receptacle 120 by processing the output of the radiation sensors 140 in response to the sequential activation of each radiation source 130 to determine which portions of the receptacle 120 contain the fluid 150.

In still other embodiments, the fluid sensing system 110 can have other arrangements. For example in selected embodiments the processor can be carried by the support structure 170 and can include the controller, discussed above, that addresses the individual radiation sources 130. In still other embodiments, the processor and/or controller can be separate from the fluid sensing system 110 and the fluid sensing system can provide unprocessed radiation sensor outputs to the processor via the signal path 178. In still other embodiments multiple radiation sensors can be positioned to receive electromagnetic radiation from each radiation source 130.

In selected embodiments, the sensing system in FIG. 1 can be made insensitive to ambient electromagnetic radiation by measuring the output of each radiation sensor 140 prior to the activation of its associated radiation source 130 and then again after the activation of the radiation source 130. For example, the output of the radiation sensor 140 can be measured prior to the activation of its corresponding radiation source 130 to determine a baseline output for the ambient light conditions. The corresponding radiation source 130 can then be activated. If the output of the radiation sensor 140 changes by at least a selected amount in response to the emitted radiation from the radiation source 130 (e.g., a photocurrent output increases by a selected amount or greater than a minimal amount above the output associated with the ambient electromagnetic radiation), it can be determined that the portion of the receptacle 120 contains fluid 150. If the output of the radiation sensor 140 does not change or changes by less than the selected amount in response to the emitted radiation from the radiation source 130, it can be determined that the portion of the receptacle proximate to the radiation source 130 does not contain fluid.

Figure 5:
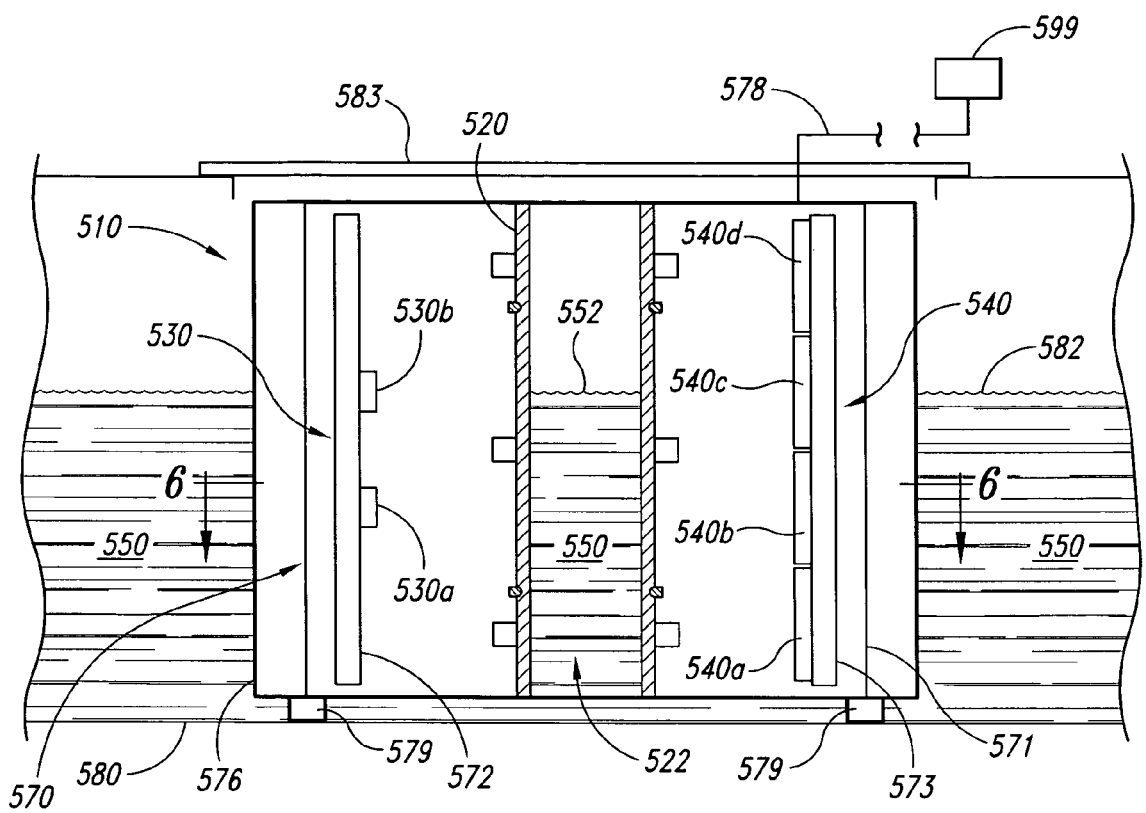
FIG. 5 is a partially schematic side elevation of a fluid system in accordance with other embodiments of the invention.
Figure 6:
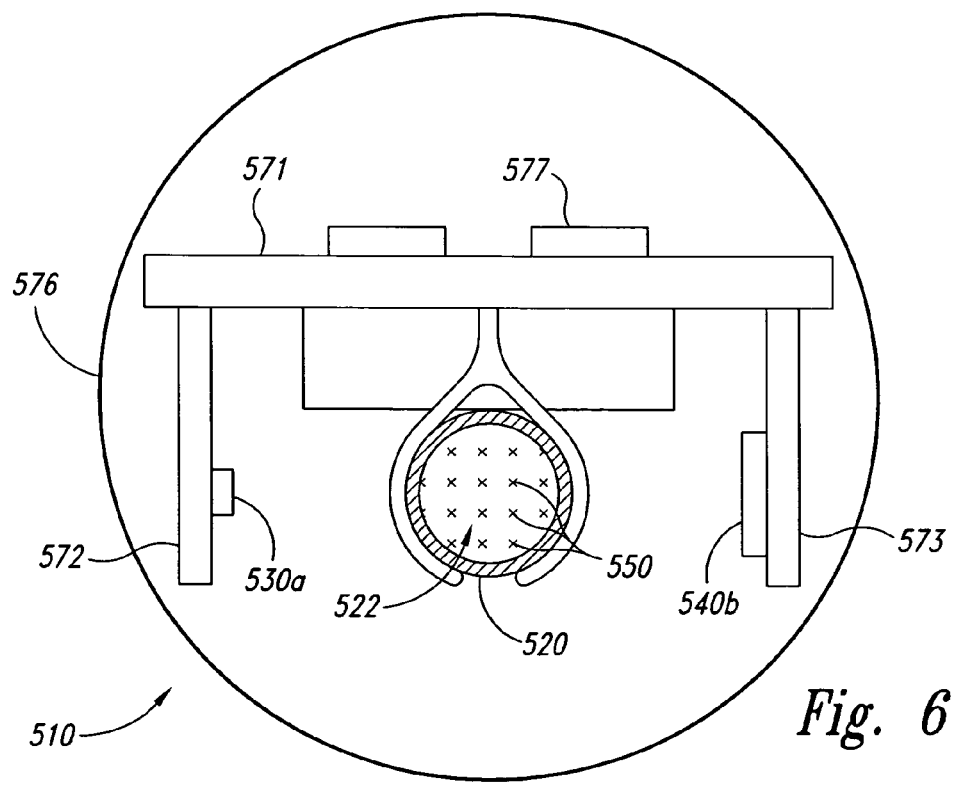
FIG. 6 is a partially schematic cross-sectional illustration of a portion of the fluid sensing system shown in FIG. 5 taken along line 6-6.

FIG. 5 is a partially schematic side elevation view of a fluid system 510 in accordance with other embodiments of the invention. FIG. 6 is a partially schematic cross-sectional illustration of a portion of the fluid sensing system 510 shown in FIG. 5 taken along line 6-6. In FIG. 5, the fluid sensing system 510 includes a receptacle 520 positioned proximate to one or more radiation sources 530 and one or more radiation sensors 540. In the illustrated embodiment, the fluid sensing system 510 includes two radiation sources 530, shown as a first radiation source 530*a* and a second radiation source 530*b*. Additionally, in FIG. 5 the fluid sensing system 510 includes four radiation sensors 540, shown as a first radiation sensor 540*a*, a second radiation sensor 540*b*, a third radiation sensor 540*c*, and a fourth radiation sensor 540*d*. In other embodiments the fluid sensing system 510 can have more or fewer radiation sources 530 and/or radiation sensors 540.

In the illustrated embodiment, the receptacle 520, radiation sources 530, and radiation sensors 540 are carried on a support structure 570. The support structure 570 includes a first support 571, a second support 572, and a third support 573, similar to the support structures discussed above with reference to FIGS. 1 and 2. In the illustrated embodiment, the support structure 570, the radiation sources 530, the radiation sensors 540, and the receptacle 520 are carried inside an enclosure 576. In FIG. 5, the fluid sensing system 510 is at least partially submerged in a fluid 550 carried by a container 580 and the receptacle 520 includes a hollow cylinder or tube that has a passageway 522 that is open at each end so that the passageway 522 is in fluid communication with the container 580. Because both ends of the passageway 522 are in fluid communication with the container 580, the fluid level 552 in the passageway 522 can be at least approximately the same as the fluid level 582 in the container 580. As described below in further detail, in various embodiments the radiation sources 530 can emit electromagnetic radiation and the fluid level 552 and/or a fluid characteristic of the fluid 550 in the passageway 520 can be determined by the characteristics of the emitted electromagnetic radiation received by the radiation sensors 540. In turn, a fluid level 582 in the container 580 and/or a fluid characteristic of the fluid in the container 180 can also be determined.

In FIG. 5, the radiation sensors 540 can be operably connected (e.g., in parallel) to a transimpedance converter 577 that turns the current output of the radiation sensors 540 into a voltage. A signal path 578 can provide power to the radiation sources 530 and/or the radiation sensors 540. Additionally, the signal path 578 can carry signals (e.g., in the form of an electrical current or voltage) from the transimpedance converter 577 to at least one other device 599 external to the fluid sensing device 510. For example, the signal path 578 can carry signals from the transimpedance converter 577 to a transmitter, processor, and/or display. In other embodiments, the fluid sensing system 510 does not include the transimpedance converter 577 and the output from the radiation sensors 540 can be carried by the signal path 578 to another device 599.

In selected embodiments, the fluid sensing system 510 shown in FIG. 5 can be inserted into a container 580 and the container 580 can be sealed by a closure device 583. In certain embodiments, the fluid sensing system 510 can be secured or restrained inside the container 580 (e.g., by a fastener or detent) to prevent movement. In other embodiments, the fluid sensing system 510 can be unrestrained in the container 580. In selected embodiments, the enclosure can include spacers 579 that can be positioned to prevent one or both open ends of the passageway 522 from being covered or blocked by an interior surface of the container 580. Although in the illustrated embodiment, the spacers 579 are only shown proximate to one end of the passageway 522, in other embodiments the spacers 579 can be located proximate to the other end or both ends of the passageway 522.

Figure 7:
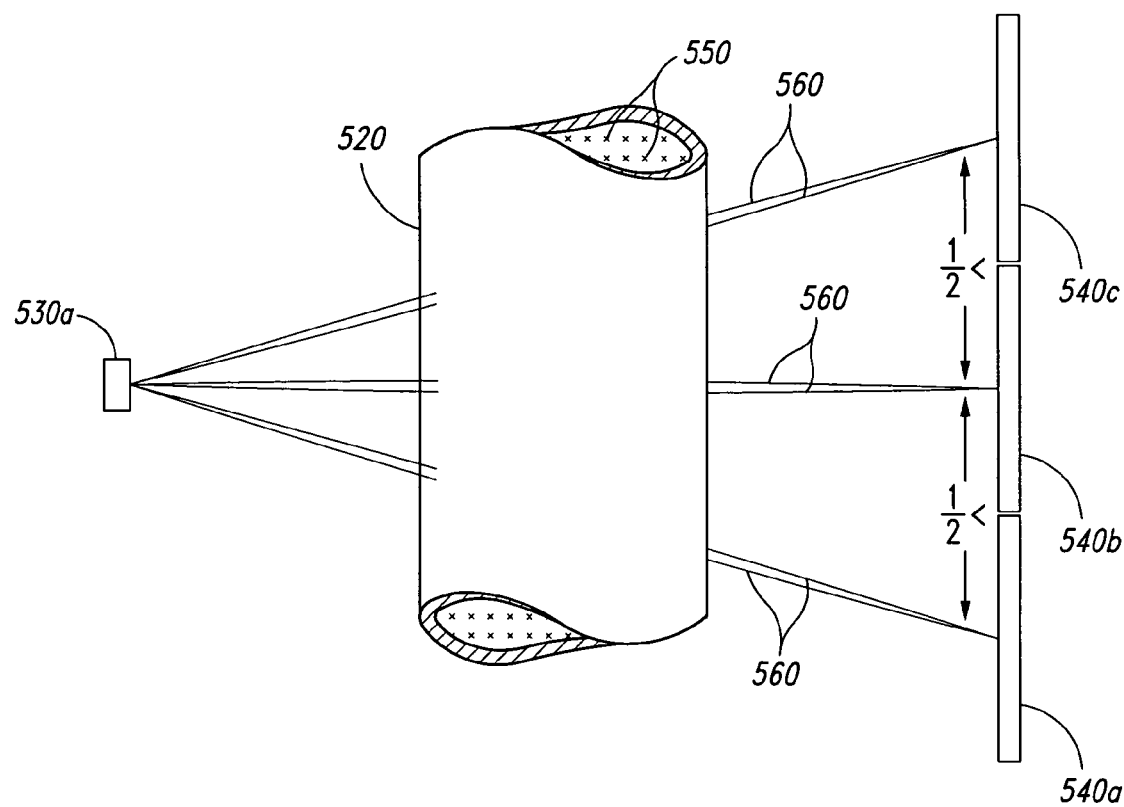
FIG. 7 is an isometric illustration of a radiation source, three radiation sensors, and a portion of a receptacle shown in FIG. 5.

In the illustrated embodiment, the radiation sources 530 can be configured to operate as quasi-Lambertian radiators that produce a column or cone of electromagnetic radiation. With quasi-Lambertian radiators a significant amount of electromagnetic radiation is produced in the forward direction (e.g., 0° from the axis of the cone) and the electromagnetic radiation approaches or falls off toward zero as the outer fringes of the cone (e.g., the half angles of the cone) are reached. For example, FIG. 7 shows the first radiation source 530a emitting a cone of electromagnetic radiation 560 through a part of the receptacle 520 filled with fluid 550. Because the receptacle 520 is filled with the fluid 550 (having a selected refractive index), the receptacle 520 acts like a cylindrical lens focusing the electromagnetic energy 560 in a vertical line that impinges on the first, second, and third radiation sensors 540a, 540b, 540c, shown in FIG. 5. As discussed above, as the half angle (½<) of the cone is reached, the emitted electromagnetic radiation in 560 falls off toward zero. As discussed above with reference to FIG. 4, portions of the receptacle 520 that do not contain the fluid 550 can cause the electromagnetic radiation 562 to refract, diffuse, or otherwise diverge so that little or no electromagnetic radiation 560 passing through the portions of the receptacle 520 that do not contain the fluid 550 is focused on the radiation sensor(s) 540. Accordingly, portions of the receptacle 520 that contain fluid 550 can be identified and/or a fluid level in the receptacle 520 can be determined.

Figure 8:
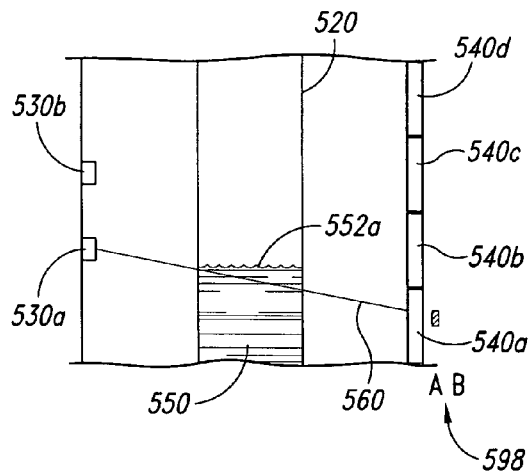
FIG. 8 is a partially schematic illustration of the operation of radiation sources and radiation sensors shown in FIG. 5 for a selected fluid level.

FIG. 8 is a partially schematic illustration of the operation of the radiation source 530 and the radiation sensors 540 shown in FIG. 5, when the fluid 550 is at a first fluid level 552a in the receptacle 520. In the illustrated embodiment, the radiation sources 530 can be operably connected (e.g., in series) to a power source and can continuously emit electromagnetic radiation 560. The radiation sensors 540 can be operably connected (e.g., in parallel) to a transimpedance converter that converts the current output of the radiation sensors 540 into a voltage. Accordingly, the combined voltage of the radiation sensors 540 can be representative of the amount of emitted electromagnetic radiation 560 received by the radiation sensors 540.

In FIG. 8, both radiation sources 530 are emitting electromagnetic radiation 560, but only a portion of electromagnetic radiation 560 emitted from the first radiation source 530a passes through a portion of the receptacle 520 that contains fluid 550 (e.g., below the first fluid level 552a). At least part of the portion of electromagnetic radiation 560 that passes through the portion of the receptacle 520 that contains fluid 550 is focused toward the first radiation sensor 540a. As discussed above, emitted electromagnetic radiation 560 that does not pass through a portion of the receptacle 520 that contains fluid 550 is dispersed. The amount of emitted electromagnetic radiation 560 that impinges on the radiation sensors 540 is shown schematically for illustrative purposes by the bar graph arrangement 598. In the bar graph arrangement 598, the amount of emitted electromagnetic radiation 560 from the first radiation source 530a that impinges on each radiation sensor 540 is shown as a vertical line in column A proximate to the respective radiation sensor 540. Emitted electromagnetic radiation 560 from the second radiation source 530b that impinges on each radiation sensor 540 is shown in column B. Accordingly, the first fluid level 552a can be determined by the total voltage that is created by the transimpedance converter in response to the output of the radiation sensors 540 based on the amount of emitted electromagnetic radiation 560 that impinges on the radiation sensors 540.

In the illustrated embodiment, the first fluid level 552a can be determined by a voltage output of the radiation sensors 540 without further processing of the signal (e.g., via the use of a voltage driven fuel gauge). Additionally, because all of the radiation sources 530 emit electromagnetic radiation 560 continually, in the illustrated embodiment there is no need for a controller that addresses the radiation sources 530 individually. Accordingly, the fluid sensing system 510 in the illustrated embodiment can be accurate and relatively simple to make and integrate into a vehicle. For example, the fluid sensing system 510 can be integrated into an unmanned aircraft similar to those described in U.S. patent application Ser. No. 10/758,943, titled METHODS AND APPARATUSES FOR CAPTURING AND STORING UNMANNED AIRCRAFT, INCLUDING METHODS AND APPARATUSES FOR SECURING THE AIRCRAFT AFTER CAPTURE, filed Jan. 16, 2004, which is fully incorporated herein by reference.

Figure 9:
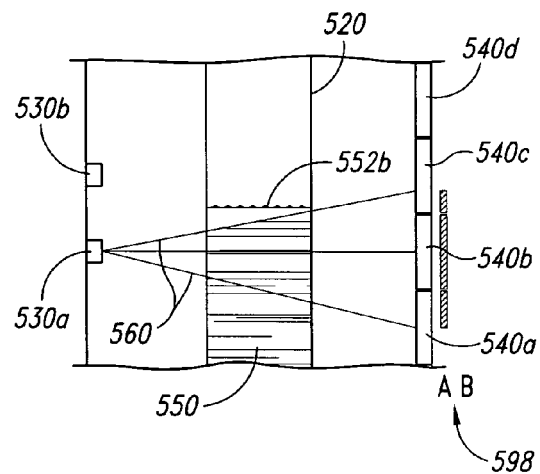
FIG. 9 is a partially schematic illustration of the operation of the radiation sources and radiation sensors shown in FIG. 8 for another fluid level.

FIG. 9 is a partially schematic illustration of the operation of the radiation sources 530 and radiation sensors 540 shown in FIG. 8 with a greater amount of fluid in the receptacle 520. Accordingly, a greater amount of electromagnetic radiation 560 emitted by the first radiation source 530a passes through portions of the receptacle 520 that contain fluid and is focused toward the radiations sensors 540. As shown by the bar graph arrangement 598, a greater amount electromagnetic radiation 560 impinges on the radiation sensors 540 (e.g., on the first, second, and third radiation sensors 540a, 540b, 540c) than did in FIG. 8. The greater amount of electromagnetic radiation 560 can produce a greater total voltage, indicating a higher second fluid level 552b in the receptacle 520. It should be noted that the lower portion of the cone of electromagnetic radiation 560 emitted by the second radiation source 530b is above the second fluid level 552b and therefore is dispersed.

Figure 10:
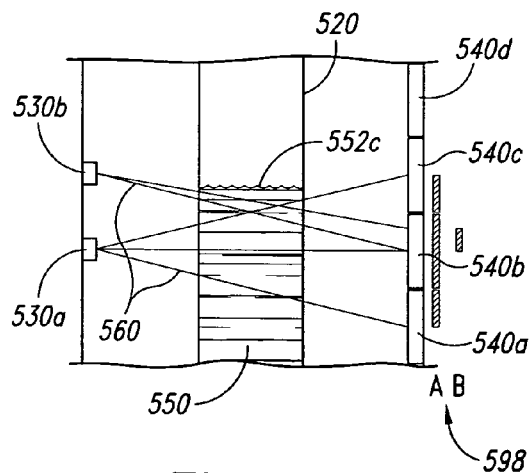
FIG. 10 is a partially schematic illustration of the operation of the radiation sources and radiation sensors shown in FIG. 9 for still another fluid level.

FIG. 10 is a partially schematic illustration of the operation of the radiation sources 530 and radiation sensors 540 shown in FIG. 9 with still a greater amount of fluid in the receptacle 520. Accordingly, a greater amount of electromagnetic radiation 560 emitted by the radiation sources 530 passes through portions of the receptacle 520 that contain fluid 550 and is focused towards the radiation sensors 540. As shown by the bar graph arrangement 598, a greater amount of electromagnetic radiation 560 impinges on the radiation sensors 540 then did in FIG. 9. For example, electromagnetic radiation 560 from the first radiation source 530a impinges on the first, second, and third radiation sensors 540a, 540b, 540c. Electromagnetic radiation 560 from the second radiation source 530b impinges on the second radiation sensor 530b. Electromagnetic radiation 560 that impinges on the receptacle 520 above a third fluid level 552c is dispersed. As indicated by the bar graph arrangement 598 the higher third fluid level 552c results in more electromagnetic radiation 560 impinging on the radiation sensors 540, causing a higher level of voltage and indicating the higher third fluid level 552c.

It should be noted that in FIG. 10 portions of electromagnetic radiation emitted from the first and second radiation sources 530a, 530b overlap on the second radiation sensor 540b, as indicated by the bar graph arrangement 598. This overlap of emitted electromagnetic radiation 560 can increase the output (e.g., increase the photocurrent) of the second radiation sensor 540b accordingly. In the illustrated embodiment, because the electromagnetic radiation 560 emitted from adjacent radiation sources 530 can overlap, a continuous measurement of the fluid level having a very fine resolution (e.g., nearly infinite or infinite resolution) can be taken when the radiation sensors 540 are spaced closely together.

Figure 11:
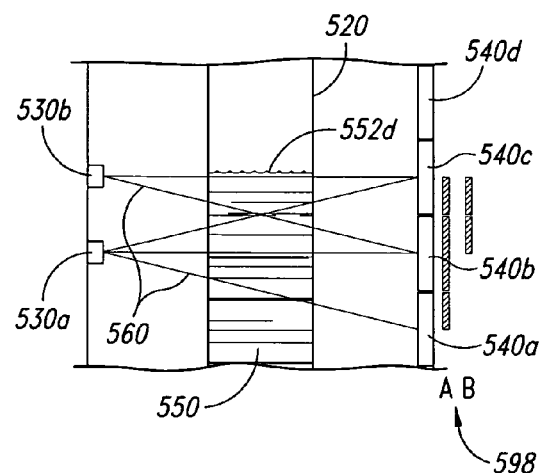
FIG. 11 is a partially schematic illustration of the operation of the radiation sources and radiation sensors shown in FIG. 10 for yet another fluid level.

FIG. 11 is a partially schematic illustration of the operation of the radiation sources 530 and radiation sensors 540 shown in FIG. 10 with yet a larger amount of fluid 550 in the receptacle 520. In FIG. 11, a higher fourth fluid level 552d allows more electromagnetic radiation 560 from the first and second radiation sources 530a, 530b to be focused toward the radiation sensors 540. As indicated by the bar graph arrangement 598, the higher fourth fluid level 552d results in more electromagnetic radiation 560 impinging on the radiation sources 540, causing a higher level of output (e.g., photocurrent) and indicating the higher fourth fluid level 552d.

In selected embodiments, the enclosure 576 (shown in FIGS. 5 and 6) can be configured to shield the radiation sensors 540 from ambient electromagnetic radiation (e.g., ambient light) to prevent ambient electromagnetic radiation levels from interfering with the determination of whether portions of the receptacle 520 contains fluid or not. For example, in selected embodiments the enclosure 576 can be opaque to prevent ambient light exterior to the enclosure 576 from impinging on the radiation sensors 540.

In other embodiments, other methods can be used to compensate for ambient electromagnetic radiation. For example, in other embodiments the enclosure does not prevent ambient electromagnetic radiation from reaching the radiation sensors 540, or the fluid sensing system 510 does not include an enclosure and the radiation sources 530 and the radiation sensors 540 are positioned proximate to the receptacle which is coupled to the container 580, similar to the configuration shown in FIGS. 1 and 2. Accordingly, the output of the radiation sensors 540 can be measured without fluid 550 in the receptacle 520 to establish an "empty" baseline with the radiation sources 530 active and with the ambient electromagnetic radiation being present. Another measurement of the radiation sensors 540 can be taken with the receptacle 520 filled with fluid 550 to establish a "full" baseline. Accordingly, radiation sensor outputs that fall between the two baselines represent various fluid levels 552 in the receptacle 520. This method is particularly well suited when the ambient level of electromagnetic radiation remains at least approximately constant during the operation of the fluid sensing system 510.

In other embodiments, the fluid sensing system 510 can have other configurations. For example, in other embodiments the fluid sensing system can include more or fewer radiation sources 530 and/or radiation sensors 540. In still other embodiments, the radiation sources 530 and/or sensors 540 can be connected in different ways, connected to additional components (e.g., various processors or controllers), or both. In yet other embodiments, the system can include a single radiation sensor that fully spans the area of interest of the receptacle (e.g., that spans the area covered by the four radiation sensors 540 shown in FIGS. 5 and 6).

In selected embodiments, a fluid sensing system can be configured to determine or sense a characteristic, or a change in characteristic, of fluid contained in a receptacle. For example, in certain embodiments the fluid sensing system can determine a characteristic of a fluid by the pattern created on a radiation sensor by emitted electromagnetic radiation that passes through a portion of the receptacle that contains the fluid. For example, FIG. 12 is a partially schematic planform view of a portion of a fluid sensing system 1210 configured to detect a characteristic of a fluid 1250 contained in a portion of a receptacle 1220 in accordance with another embodiment of the invention.

Figure 12:
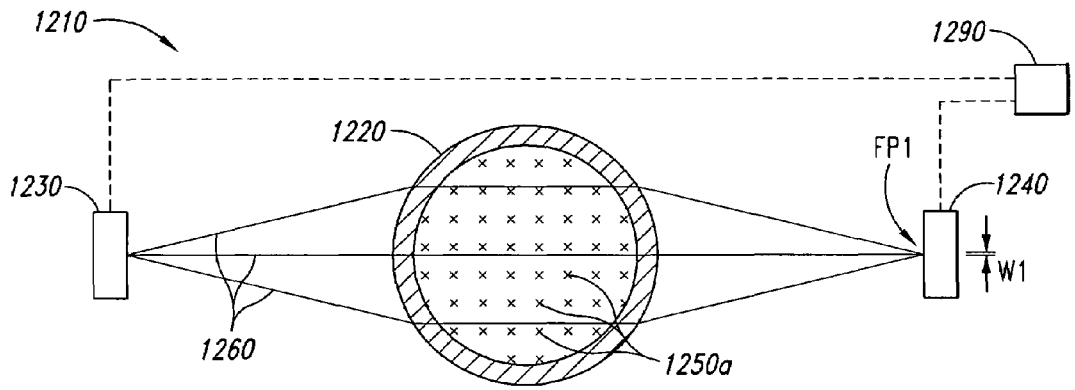
FIG. 12 is a partially schematic illustration of a portion of a fluid sensing system in accordance with another embodiment of the invention.

In FIG. 12, the fluid sensing system 1210 includes one or more radiation sources 1230 positioned to emit electromagnetic radiation through a portion of the receptacle 1220 filled with a first fluid 1250a. The receptacle can be configured to act as a cylindrical lens in a manner generally similar to that described above. For the purpose of illustration only a single radiation source 1230 and a single radiation sensor 1240 are shown, however, in other embodiments the fluid sensing system 1210 can have more radiation sources 1230 and/or radiation sensors 1240.

As described above with reference to FIG. 7, in selected embodiments the cylindrical lens can focus a line toward the one or more radiation sensors 1240 based on the size and shape of the cone(s) of electromagnetic radiation 1260 emitted by the radiation source 1230. The width of the line or pattern that impinges on the radiation sensor 1240 can depend on whether the electromagnetic radiation 1260 has a first focal point FP1 in front of, on, or behind the radiation sensor 1240. Changes in the refractive index of the first fluid 1250a can change the location of the first focal point FP1, which in turn can vary the pattern of electromagnetic radiation that impinges on, or is created on, the radiation sensor 1240.

Accordingly, the radiation sensor 1240 shown in FIG. 12 can be configured to detect different patterns that can be related to the changes in the refractive index of the fluid carried in the receptacle 1220.

Figure 13:
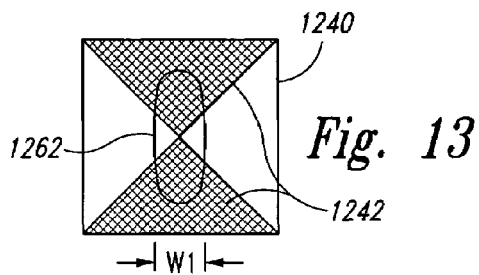
FIG. 13 is a partially schematic illustration of a sensor suitable for use in the portion of the fluid sensing system shown in FIG. 12.
Figure 14:
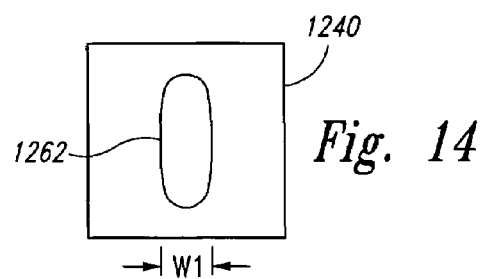
FIG. 14 is a partially schematic illustration of another sensor suitable for use in the portion of the fluid sensing system shown in FIG. 12.

The radiation sensor 1240 shown in FIG. 12 can include various types of spatially sensitive detectors. For example, in certain embodiments the radiation sensor 1240 shown in FIG. 12 can include a masked photodetector or masked photodiode as shown in FIG. 13. In FIG. 13, the masked photodetector includes a photodetector that has two triangular coverings 1242 positioned to cover at least approximately half of the electromagnetic radiation sensing area of the photodetector. The coverings 1242 can be configured so that selected wavelengths of electromagnetic radiation emitted by the radiation source 1230 cannot pass through the coverings 1242. As discussed in further detail below, the coverings 1242 can be positioned so that the wider the pattern of emitted electromagnetic radiation that impinges on the photodetector, the more electromagnetic radiation the photodetector will sense. Accordingly, the masked photodetector can sense the width of the pattern created by the electromagnetic radiation 1260. In other embodiments, the radiation sensor 1240 shown in FIG. 12 can include a pixilated array that can detect pattern characteristics as shown in FIG. 14. For example, the radiation sensor 1240 can include a CCD or CID device having an array of pixels that can sense pattern characteristics, including width, length, and/or the like.

In FIG. 12 the first focal point is close to, or at, the surface of the radiation sensor 1240. Accordingly, the pattern the electromagnetic radiation produces on the surface of the radiation sensor 1240 can be relatively narrow. For example, as shown in FIG. 13 the pattern can have a first width W1 and only a small portion of the electromagnetic radiation impinges on a portion of the radiation sensor 1240 that is not covered by the coverings 1242. In FIG. 14, the pixilated array can sense the first width W1 of the pattern via the pixel array.

Figure 15:
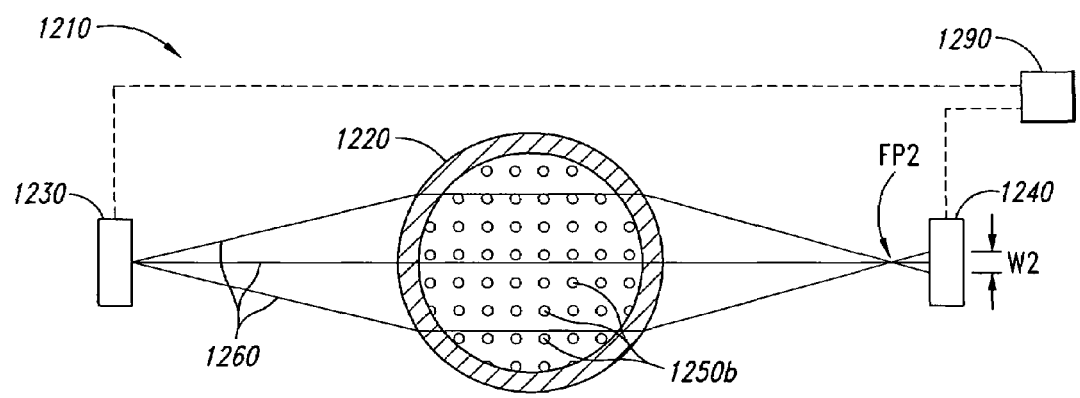
FIG. 15 is a partially schematic illustration of the portion of the fluid sensing system shown in FIG. 12, with a different fluid.

FIG. 15 is a partially schematic illustration of the portion of the fluid sensing system 1210 shown in FIG. 12, with a second fluid 1250*b* carried by the portion of the receptacle 1220. The second fluid 1250*b* has a different refractive index than the first fluid 1250*a*. For example, in a selected embodiment the second fluid 1250*b* can have a different molecular composition (e.g., the second fluid 1250*b* and be a different grade of fuel than the first fluid 1250*a*) with a different refractive index. In other embodiments the second fluid 1250*b* can be generally the same as the first fluid 1250*a*, but can include contaminants (e.g., water), debris, or bubbles that alter the refractive index. Because the second fluid 1250*b* has a different refractive index than the first fluid 1250*a*, the electromagnetic radiation 1260 emitted from the radiation source 1230 that passes through the fluid filled portion of the receptacle 1220 is focused toward a second focal point FP2.

Figure 16:
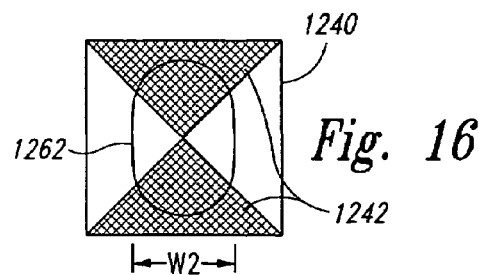
FIG. 16 is a partially schematic illustration of a pattern created on the sensor shown in FIG. 13 with the different fluid.
Figure 17:
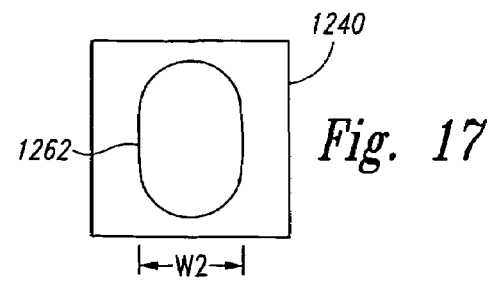
FIG. 17 is a partially schematic illustration of the pattern created on the sensor shown in FIG. 14 with the different fluid.

As shown in FIG. 15, the second focal point FP2 is in front of the radiation sensor 1240. Accordingly, a wider pattern is created on the radiation sensor 1240 by the electromagnetic radiation 1260. For example, FIG. 16 is a partially schematic illustration of the pattern created on the masked photodetector discussed above with reference to FIG. 13. In FIG. 16, the pattern created by the emitted electromagnetic radiation 1260 that passes through the portion of the receptacle 1220 containing the second fluid 1250*b* has a second width W2 that is larger than the first width W1 (shown in FIG. 13). As shown in FIG. 16, the wider pattern can allow more emitted electromagnetic radiation 1260 to impinge on the portion of the photodetector that is not covered by the coverings 1242. Accordingly, the masked photodetector can sense that the pattern created by the emitted electromagnetic radiation 1260 has the second width W2. Similarly, if the radiation sensor 1240 includes a pixilated array as shown in FIG. 17, the pixilated array can sense the second width W2. As discussed above, the different pattern widths can indicate that the fluids in the receptacle have different characteristics.

In selected embodiments, the portion of the fluid sensing system 1210, shown in FIGS. 12 and 15 can include, or be operably coupled to a processor 1290 that provides input to the radiation sources 1230 (e.g., the processor can include a controller) and/or receives outputs from the radiation sensors 1240 for processing. In other embodiments, the portion of the fluid sensing system 1210 shown in FIGS. 12 and 15 can have other arrangements. For example, in selected embodiments the fluid sensing system 1210 can include different shaped receptacles 1220 that cause the emitted electromagnetic radiation 1260 to create different pattern characteristics on the radiation sensors 1240 when passing through the receptacle 1220 that contains a fluid. In certain embodiments, the portion of the fluid sensing system 1210 can be a portion of a fluid sensing system that also determines a fluid level in the receptacle 1220, as discussed above with reference to FIGS. 1-11. For example, when the radiation sensor includes a CCD or CID that is configured to sense a pattern characteristic, the radiation sensor can be used to determine a fluid characteristic and to determine if a portion of the receptacle contains a fluid.

Figure 18:
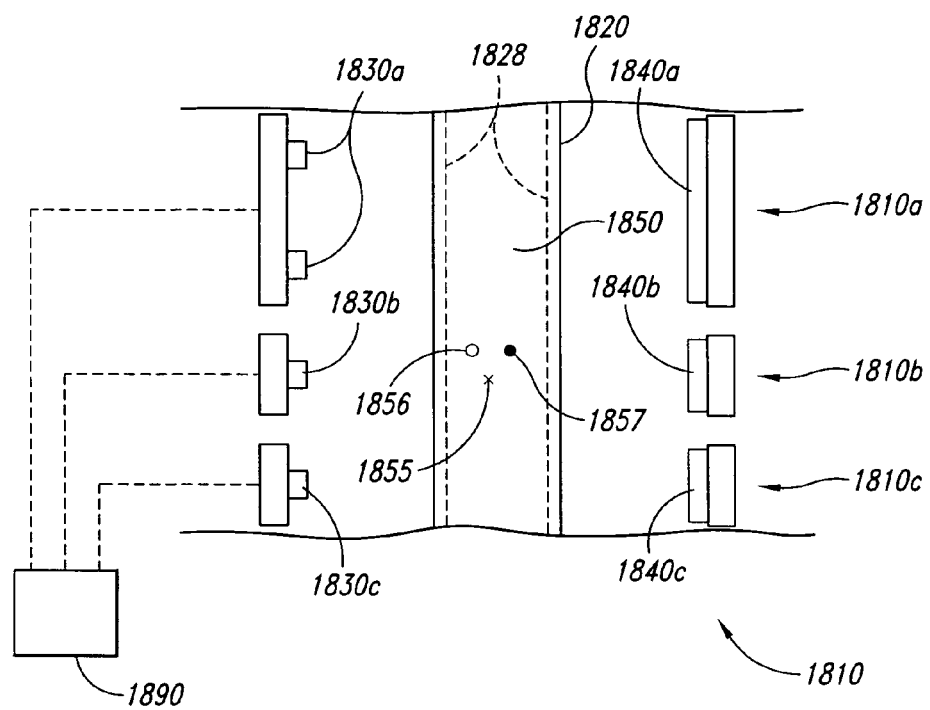
FIG. 18 is a partially schematic illustration of multiple fluid sensing systems operably coupled to a processor in accordance with other embodiments of the invention.

FIG. 18 is a partially schematic illustration of multiple fluid sensing systems 1810 operably coupled together in accordance with other embodiments of the invention. In FIG. 18, three fluid sensing systems 1810 are shown as a first fluid sensing system 1810*a*, a second fluid sensing system 1810*b*, and a third fluid sensing system 1810*c*. The first fluid sensing system 1810*a* can be configured to sense a fluid height in a portion of a receptacle 1820, similar to the fluid sensing system discussed above with reference to FIGS. 5 and 6. In the illustrated embodiment, the first fluid sensing system 1810*a* includes two radiation sources 1830*a* and a single radiation sensor 1840*a* that is positioned to receive the electromagnetic radiation emitted by both the radiation sources 1830*a*.

The second fluid sensing system 1810*b* can be configured to sense a fluid characteristic, similar to the fluid sensing system discussed above with reference to FIGS. 12-17. In the illustrated embodiment, the second fluid sensing system 1810*b* includes a single radiation source 1830*b* and a single masked photodetector 1840*b*. The masked photodetector 1840*b* can be configured to sense a change in a pattern of emitted electromagnetic radiation caused by a change in a characteristic of a fluid 1850 (e.g., a molecular composition 1855, a contaminant 1855 or debris, and/or bubbles 1856).

Because in some embodiments the masked photodetector 1840*b* relies on sensing an amount of emitted electromagnetic radiation, it can be important to know if electromagnetic radiation passing through the receptacle and the fluid is being attenuated. For example, over time a coating 1828 can build up in the receptacle that can attenuate various wavelengths of electromagnetic radiation. Accordingly, the third fluid sensing system 1810*c* (e.g., a reference sensing system) can be configured to sense how much the electromagnetic radiation passing through the receptacle and fluid is being attenuated.

In the illustrated embodiment, the third fluid sensing system 1810*c* includes a radiation source 1830*c* and a radiation sensor 1840*c*. The radiation source 1830*c* can include a radiation source that is similar to the radiation source 1830*b* of the second fluid sensing system 1810*b*. Additionally, in FIG. 18 the radiation sensor 1840*c* can include a photodetector similar to the photodetector used to make the masked photodetector 1840*b* in the second fluid sensing system 1810*b*, but without the coverings. Accordingly, the total amount of electromagnetic radiation received by radiation sensor 1840*c* of the third fluid sensing system 1810*c* can be compared (e.g., ratiometrically) to the electromagnetic radiation sensed by the masked photodetector 1840*b* of the second fluid sensing system 1810b to determine the percentage of electromagnetic radiation being blocked by the coverings of the masked photodetector 1840b of the second fluid sensing system 1810b. Accordingly, a pattern characteristic (e.g., pattern width), corrected for electromagnetic radiation attenuation, can be also determined.

In the illustrated embodiment, the first, second, and third 1810a, 1810b, 1810c fluid sensing systems can be coupled together via a processor 1890. For example, the processor 1890 can compare (e.g., ratiometrically) the output of the third fluid sensing system 1810c to the output of the second fluid sensing system 1810b and can provide compensation for any electromagnetic attenuation caused by the coating 1828. In other embodiments, the coupled fluid sensing systems 1810 shown in FIG. 18 can have other arrangements. For example, in other embodiments one or more fluid sensing systems 1810 can be coupled together without the use of a processor (e.g., multiple fluid sensing systems 1810 similar to the first fluid system 1810a can be coupled together without the use of a processor).

Figure 19:
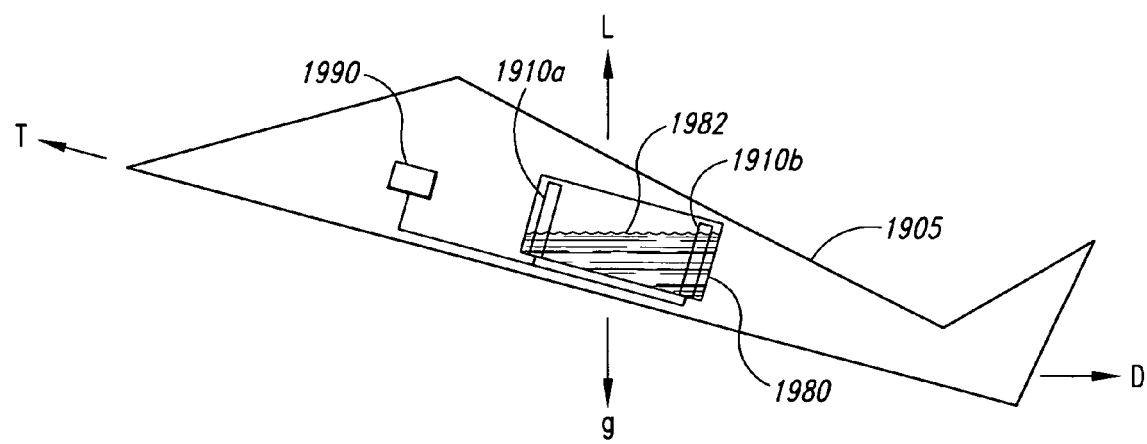
FIG. 19 is a partially schematic illustration of a vehicle carrying multiple fluid sensing systems operably coupled to a processor in accordance with still other embodiments of the invention.

FIG. 19 is a partially schematic illustration of a vehicle 1905 (e.g., an aerospace vehicle) carrying multiple fluid sensing systems 1910, shown as a first fluid sensing system 1910a and a second fluid sensing system 1910b, in accordance with yet another embodiment of the invention. In the illustrated embodiment, the first and second fluid sensing systems 1910a, 1910b are operably coupled together via a processor 1990. The first and second fluid sensing systems 1910a, 1910b can be configured to measure the fluid levels in separate portions of a container 1980 (e.g., a fuel tank). The processor 1990 can process the output (e.g., process an electrical current characteristic) from the first and second fluid sensing systems 1910a, 1910b to determine a fluid level 1982 in the container. For example, as the fluid in the container 1980 shifts due to various accelerations (e.g., lift L, drag D, thrust T, and gravity g), the processor can average the outputs from the first and second fluid sensing systems 1910a, 1910b to determine the fluid level 1982 in the container 1980. In other embodiments, the process can average the output over a selected period of time to compensate for momentary changes in fluid placement/movement. In further embodiments, the processor 1990 can include a transmitter for transmitting the processed information to a remote site.

A feature of some of the embodiments discussed above is that a fluid sensing system can be made smaller and lighter than current systems that are used in vehicles to measure fluid levels, such as fuel levels in fuel tanks. An advantage of this feature is that weight and space can be saved, providing for smaller and lighter vehicles to meet various operational needs. Another feature of some of the embodiments discussed above is that the amount of electrical components exposed to fuel vapors can be reduced as compared to current systems. An advantage of this feature is that the risk of explosion can be reduced in some cases, thereby increasing operational safety. Still another feature of some of the embodiments discussed above is that a fluid characteristic can be sensed. An advantage of this feature is that in some cases fuel contaminants and/or an inappropriate grade of fuel can be sensed in time to take corrective action.

From the foregoing, it will be appreciated that specific embodiments of the invention have been described herein for purposes of illustration, but that various modifications may be made without deviating from the invention. Additionally, aspects of the invention described in the context of particular embodiments may be combined or eliminated in other embodiments. For example, although aspects of the present invention have been described above with reference to sensing a fluid level or characteristic in a container by sensing a fluid level or characteristic in an attached receptacle, in other embodiments the receptacle itself can serve as a fluid container or reservoir and the system can determine a fluid characteristic and/or whether selected portions of the receptacle contain a fluid. Although advantages associated with certain embodiments of the invention have been described in the context of those embodiments, other embodiments may also exhibit such advantages. Additionally, not all embodiments need necessarily exhibit such advantages to fall within the scope of the invention. Accordingly, the invention is not limited except as by the appended claims.

I claim:

1. A fluid sensing system, comprising:
a receptacle positioned to contain a fluid;
at least one radiation source positioned to emit electromagnetic radiation through the receptacle; and
at least one radiation sensor positioned to receive a portion of the emitted electromagnetic radiation that passes through the receptacle, wherein the at least one radiation source and the at least one radiation sensor define, at least in part, a radiation path, and wherein the receptacle is positioned so that electromagnetic radiation that passes along the radiation path through portions of the receptacle containing fluid is focused to impinge on the at least one radiation sensor so that more emitted electromagnetic radiation is received by the at least one radiation sensor through portions of the receptacle that contain fluid than through portions that do not contain fluid,
wherein the receptacle includes sidewalls having a generally uniform thickness along the radiation path, and
wherein an internal volume of the receptacle along the radiation path between the radiation source and the radiation sensor is generally hollow and uninterrupted.

2. The system of claim 1 wherein the receptacle contains fluid and the fluid includes a liquid fuel.

3. The system of claim 1 wherein the at least one radiation source emits electromagnetic radiation and the electromagnetic radiation includes light.

4. The system of claim 1 wherein the at least one radiation sensor is positioned to determine a fluid level within the receptacle.

5. The system of claim 1 wherein:
the receptacle includes a first side, a second side, and a passageway positioned to contain the fluid, wherein the passageway is positioned between the first and second sides;
the at least one radiation source is positioned exterior to the receptacle and proximate to the first side of the receptacle; and
the at least one radiation sensor is located exterior to the receptacle and proximate to the second side, at least a portion of the emitted electromagnetic radiation that passes through the receptacle passing through the first side, the passageway, and the second side of the receptacle.

6. The system of claim 1, further comprising a processor, the processor being operably coupled to the at least one radiation sensor and configured to process a characteristic of a signal transmitted by the radiation sensor.

7. The system of claim 1 wherein:
the at least one radiation sensor includes multiple radiation sensors; and
the at least one radiation source includes multiple radiation sources, and wherein the system further comprises a controller coupled to the multiple radiation sensors to individually activate the multiple radiation sources.

8. The system of claim 1, further comprising a processor configured to process outputs from the at least one radiation sensor over a period of time.

9. The system of claim 1, further comprising a processor configured to process outputs from the at least one radiation sensor with outputs from another fluid sensing system.

10. The system of claim 1 wherein the receptacle, radiation source and radiation sensor are positioned on an aerospace vehicle.

11. The system of claim 1 wherein:
the at least one radiation source includes multiple radiation sources;
the at least one radiation sensor includes multiple radiation sensors;
the receptacle, radiation sources, and radiation sensors are positioned on an aircraft;
the receptacle is in fluid communication with a fuel tank of the aircraft, and wherein the receptacle is positioned outside of a periphery of the fuel tank; and
the system further comprises a processor operably coupled to at least one radiation sensor, wherein the processor is configured to process outputs from the radiation sensors; and
process instructions to compensate for at least one of momentary changes in fluid placement and fluid movement caused by one or more accelerations of the aircraft.

12. A fluid sensing system, comprising:
means for passing electromagnetic radiation along a radiation path and through a receptacle positioned to hold a fluid, wherein the receptacle includes sidewalls having a generally uniform thickness along the radiation path, and wherein an internal portion of the receptacle along the radiation path is generally hollow and unobstructed, and further wherein the receptacle is configured so that electromagnetic radiation that passes through portions of the receptacle containing fluid is focused; and
means for determining whether fluid is located in a selected portion of the receptacle based on an amount of electromagnetic radiation that impinges on at least one radiation sensor after passing through the selected portion of the receptacle.

13. The system of claim 12 wherein the receptacle contains fluid and the fluid includes a liquid fuel.

14. The system of claim 12 wherein the means for passing electromagnetic radiation passes light through the receptacle.

15. The system of claim 12 wherein the means for determining whether fluid is located in a selected portion of the receptacle includes a means for determining whether fluid is located in multiple selected portions of the receptacle.

16. The system of claim 12, further comprising a processor coupled to the means for determining to process outputs from the means for determining.

17. The system of claim 12 wherein the fluid sensing system is configured to be installed in an aerospace vehicle.

18. The system of claim 12 wherein the system further comprises:
a radiation source positioned to emit electromagnetic radiation through the receptacle; and
the one or more radiation sensors are positioned to receive a portion of the emitted electromagnetic radiation that passes from the radiation source through the receptacle, an output of the one or more radiation sensors being suitable for comparison with an output of the means for determining.

19. An aerospace system, comprising:
an aerospace vehicle; and
a fluid sensing system carried by the aerospace vehicle, the fluid sensing system comprising:
a receptacle positioned to contain a fluid;
a radiation source positioned to emit electromagnetic radiation through the receptacle; and
a radiation sensor positioned to receive a portion of the emitted electromagnetic radiation that passes through the receptacle, wherein the radiation source and the radiation sensor define, at least in part, an optical path, and wherein the receptacle is positioned so that electromagnetic radiation that passes along the optical path through portions of the receptacle containing fluid is focused to impinge on the radiation sensor so that more emitted electromagnetic radiation is received by the radiation sensor through portions of the receptacle that contain fluid than through portions that do not contain fluid, an output of the at least one radiation sensor being usable to determine a fluid level in the aerospace vehicle,
wherein the receptacle includes sidewalls having a generally uniform thickness alone the optical path, and
wherein an internal volume of the receptacle along the optical path between the radiation source and the radiation sensor is generally hollow and unobstructed.

20. The system of claim 19 wherein the aerospace vehicle includes an unmanned aerospace vehicle.

21. The system of claim 19 wherein the receptacle positioned to contain a fluid includes a receptacle positioned to contain a fuel.

22. The system of claim 19 wherein the at least one radiation source emits electromagnetic radiation and the electromagnetic radiation includes light.

23. The system of claim 19 wherein the at least one radiation sensor is positioned to determine a fluid level within the receptacle.

24. The system of claim 19, further comprising a processor configured to process outputs from the at least one radiation sensor with outputs from another fluid sensing system carried by the aerospace vehicle.

* * * * *